United States Patent (10) Patent No.: US 8,858,769 B2
Kurose et al. (45) Date of Patent: Oct. 14, 2014

(54) KARL FISCHER TITRATOR AND KARL FISCHER TITRATION METHOD (75) Inventors: Ikumi Kurose, Kyoto (JP); Masaaki Ishikura, Kyoto (JP)

(73) Assignee: Kyoto Electronics Manufacturing Co., Ltd., Kyoto (JP)

( * ) Notice: Subject to any disclaimer, the term of this patent is extended or adjusted under 35 U.S.C. 154(b) by 0 days.

(21) Appl. No.: 13/979,734

(22) PCT Filed: Feb. 14, 2012

(86) PCT No.: PCT/JP2012/000946
§ 371 (c)(1),
(2), (4) Date: Jul. 15, 2013

(87) PCT Pub. No.: WO2012/111306
PCT Pub. Date: Aug. 23, 2012

(65) Prior Publication Data
US 2014/0001057 A1 Jan. 2, 2014

(30) Foreign Application Priority Data
Feb. 18, 2011 (JP) ................. 2011-033621

(51) Int. Cl.
*G01N 27/44* (2006.01)
*G01N 27/42* (2006.01)
*G01N 31/16* (2006.01)

(52) U.S. Cl.
CPC ............ *G01N 27/423* (2013.01); *G01N 31/168* (2013.01); *G01N 27/44* (2013.01)
USPC .......... 204/405; 205/788; 205/788.5

(58) Field of Classification Search
CPC ....... G05D 21/02; G01N 27/44; G01N 27/42; G01N 27/06; G01N 27/423; G01N 31/164; G01N 31/16; G01N 31/168
USPC .......... 204/405, 406; 205/788.5, 788; 436/51, 436/42; 422/75, 76; 324/425
See application file for complete search history.

(56) References Cited

U.S. PATENT DOCUMENTS

| 4,211,614 A | 7/1980 | Eppstein et al. |
| 4,368,105 A * | 1/1983 | Muroi et al. ................ 205/788 |
| 5,296,193 A | 3/1994 | Reger et al. |
| 6,361,670 B1 * | 3/2002 | Cedergren ................ 204/405 |

FOREIGN PATENT DOCUMENTS

| JP | 55-24652 A | 2/1980 |
| JP | 1-260362 A | 10/1989 |
| JP | 6-308113 A | 11/1994 |
| JP | 2000-356621 A | 12/2000 |
| JP | 2007-278919 A | 10/2007 |

OTHER PUBLICATIONS

Metrohm, "851 Titrando / 852 Titrando", Document # 8.851.5001 EN, publiahed Apr. 2010.*

(Continued)

*Primary Examiner* — J. Christopher Ball
(74) *Attorney, Agent, or Firm* — Birch, Stewart, Kolasch & Birch, LLP (57) ABSTRACT

In the invention, a back titration and titer determination can be made using a back coulometric titration. When the iodine exists in a solution put in the titration flask with electrolytic electrodes, a back coulometric titration is performed to produce iodine ions from the iodine at the anode of the electrolytic electrodes. Where the solution is a dehydrated solvent including a Karl Fischer reagent for a volumetric titration, the titer can be determined by the back coulometric titration. Where the solution is anolyte in which the iodine remains after the coulometric titration in the coulometric titration method, the water content in the sample is found from the quantity of electricity consumed by the coulometric titration and the quantity of electricity consumed by the back coulometric titration. Where the solution is anolyte in which the iodine remains by adding Karl Fischer reagent in the volumetric titration method, the water in the sample put in the titration flask is found from the added amount of Karl Fischer reagent and the quantity of electricity consumed by the back coulometric titration.

12 Claims, 9 Drawing Sheets

(56) References Cited

OTHER PUBLICATIONS

Katoh et al., "Determination of Water in Pharmaceuticals by Back-Titration of the Karl Fischer Volumetric Titration", Study of Medical Supplies, vol. 30, No. 6, pp. 285-288, Jun. 20, 1999.

Schatch, E. "A Modern Karl Fischer Titrator" 2403 International Laboratory, Fairfield Conn. 14:2:65-70 (1984).

Torsiensson, L.-G., "Controlled-Potential Back-Titration with Electrogenerated Iodine as an Intermediate: Application to the Determination of Thiols", Talanta, Pergamon Press, Great Britain, 20:1319-1328.

* cited by examiner

KARL FISCHER TITRATOR AND KARL FISCHER TITRATION METHOD

TECHNICAL FIELD

The invention relates to Karl Fischer titration method using a Karl Fischer titration apparatus, and, in particular, to a Karl Fischer titration method using a Karl Fischer titration apparatus for a titer determination and a back titration by means of coulometric titration.

BACKGROUND ART

As a method for measuring water content by means of Karl Fischer titration method, there are a volumetric titration method and a coulometric titration method, and there are apparatus corresponding to each method.

Figure 8:
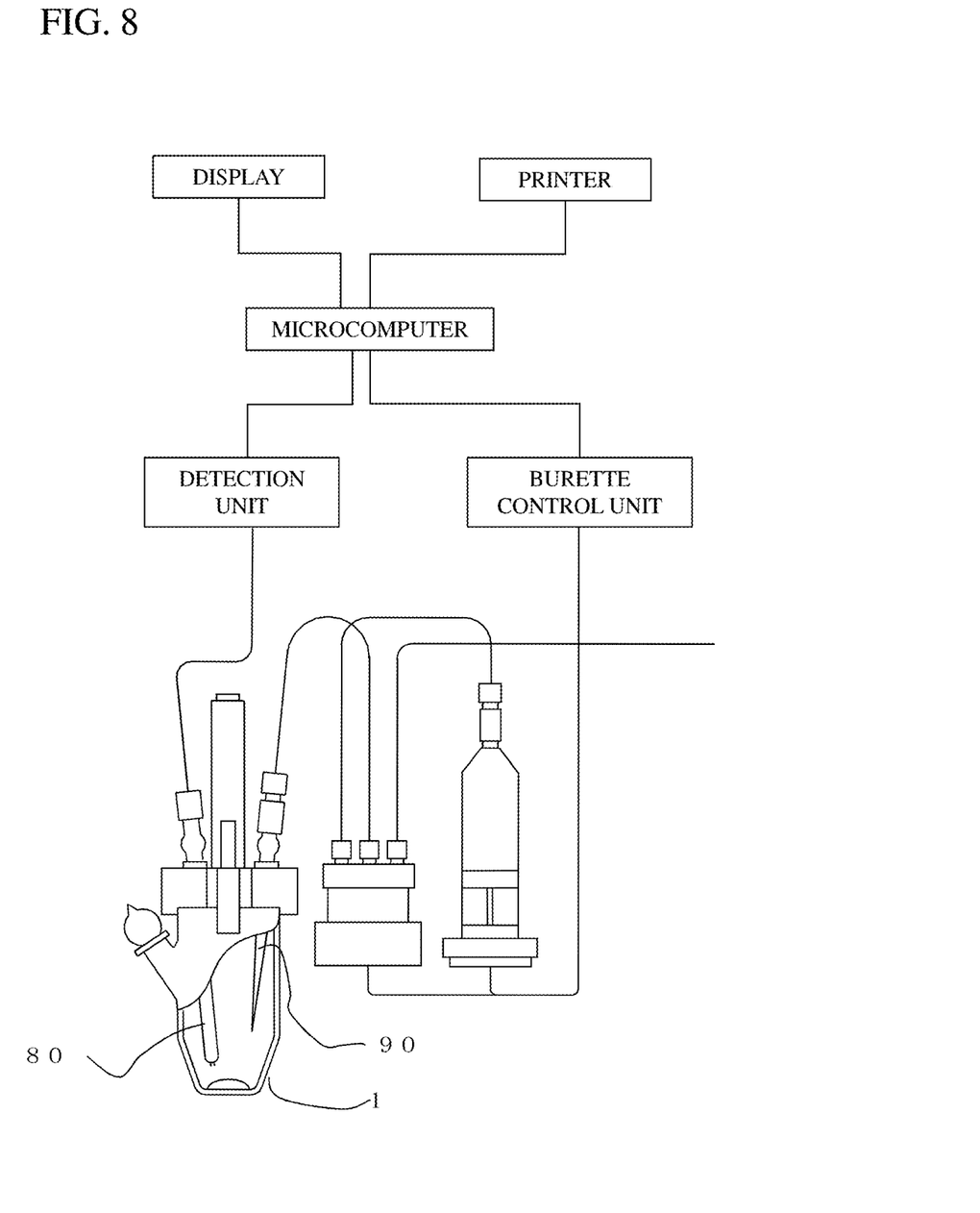
FIG. 8 is a conventional volumetric titration apparatus.

The volumetric titration apparatus has a basic configuration as shown in FIG. 8, wherein a titration flask 1 is provided with an injection nozzle 90 for titrating Karl Fischer reagent and an detection electrode 80 for detecting a polarization state. In such configuration, a dehydrated solvent is put in the titration flask 1, which is dehydrated by performing a preliminary titration with the Karl Fischer reagent. In this condition, a sample is put in the titration flask 1, and then drops of Karl Fisher reagent are added therein. According such process, the water contained in the sample reacts with iodine in the reagent. Since a concentration of iodine increases and a voltage detected by the detection electrode 80 falls as the reagent is added therein, a point when the detected voltage becomes a specific value is set to an end point. In this case, since the added amount of the reagent reacts quantitatively with the water content, the water content in the sample can be estimated by the added amount of the reagent.

In order to establish the above-mentioned theory, since it is based on the assumption that the water amount reacting with a specific amount (e.g. 1 ml) of Karl Fischer reagent (which is referred to titer) is known in advance, the titer of the reagent to be used is necessary to be measured previously. This measurement uses a liquid to be standard, such as a standard solution. That is, the standard solution (water produced as standard solution, sodium tartrate dihydrate, and pure water) is injected in the titration flask 1 holding the dehydrated solvent, and Karl Fischer reagent is added therein, so that the water amount reacting with the standard solution is defined as the titer.

In the above volumetric titration, the used Karl Fischer reagent is disposed as matters now standard, because it is no further use for the titer determination as described later.

Figure 9:
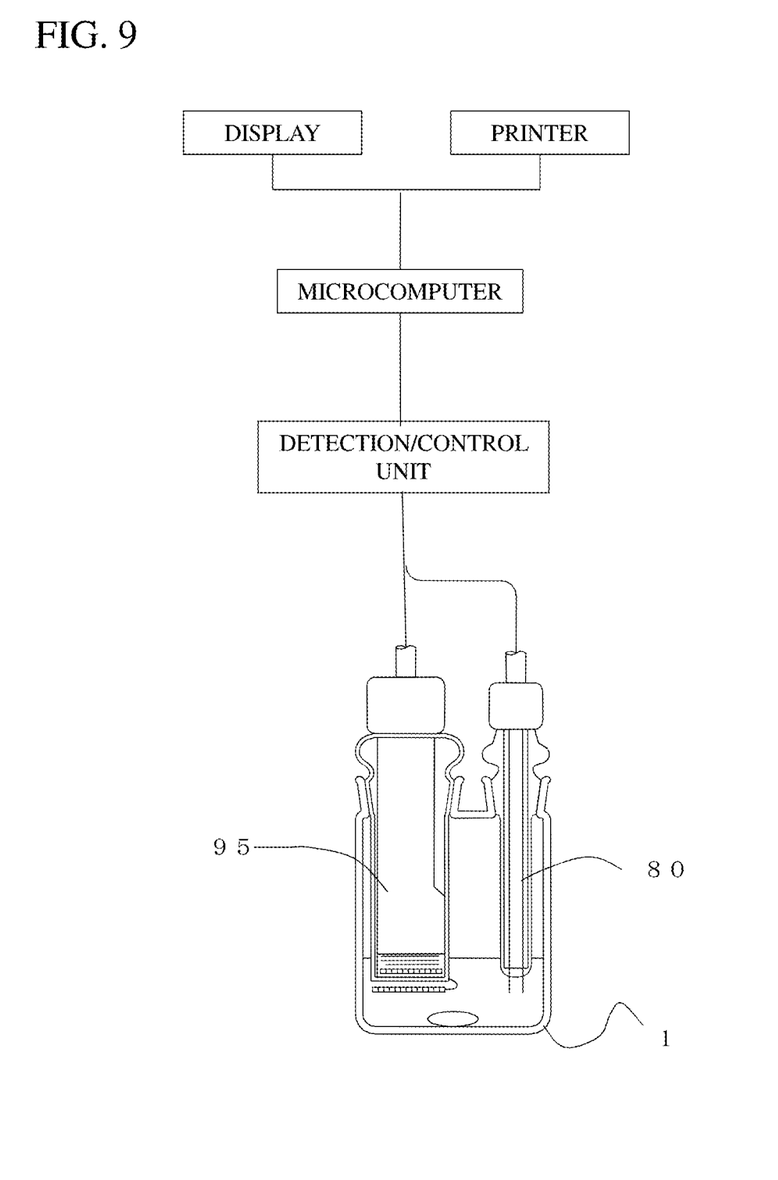
FIG. 9 is a conventional coulometric titration apparatus.

In the coulometric titration apparatus, the titration flask 1 is provided with an electrolytic electrode 95 for electrolytic treatment of anolyte, and the detection electrode 80 for detecting the polarization state, as shown in FIG. 9.

In the configuration, the anolyte (solution including iodine ions) is put in the titration flask 1 and catholyte is put in a chamber of the electrolytic electrode 95. Since the anolyte absorbs humidity in the air at this time, the anolyte is dehydrated by the electrolytic treatment for generating the iodine at the electrolytic electrode 95 (the preliminary titration). In this condition, the sample is put in the anolyte, and the electrolytic treatment is carried out at the electrolytic electrode 95 to produce the iodine from the iodine ions, and make the iodine react with the water in the sample, (the titration for producing the iodine from the iodine ions is referred to the coulometric titration, hereinafter).

As the coulometric titration proceeds, the concentration of iodine in the titration flask 1 increases and the voltage detected by the detection electrode 80 reduces, therefore a point when the detected voltage becomes a specific value is set to an end point. The water content can be estimated based on the quantity of electricity consumed at this time.

The coulometric titration used here is an electric current control method for controlling voltage so as to fix the current to a constant, and the results by means of the current control method are well-matched with theoretical values, as long as the iodine is produced from the iodine ions.

In the above-mentioned volumetric titration apparatus, a back titration as described hereinafter can be carried out.

Specifically, the iodine in Karl Fischer reagent reacts with the water in the sample as described above. A specific amount of Karl Fischer reagent (water equivalent x) is added in the sample. When the reaction of the water in the sample and the iodine is terminated, the iodine that did not react with the water in the sample has remains, so that the detection electrode 80 indicates a lower value than the end point. Accordingly, when a standard water-methanol is titrated in this condition, the standard water-methanol reacts with the excessive iodine and the iodine ions are produced. When the standard water-methanol is added up to that the voltage indicated by the detection electrode 80 becomes the end point, the water content in the sample can be calculated by x−y, based on the added amount of the standard water-methanol (water equivalent y) and the amount of the Karl Fischer reagent (water equivalent x).

The titration for producing the iodine ion from the iodine in this case, however, is limited to the volumetric titration method. This kind of titration cannot be carried out in the coulometric titration apparatus due to the reasons described later, and the coulometric titration apparatus cannot be applied to the back titration. Moreover, since the coulometric titration apparatus is not provided with a burette for adding the standard water-methanol and the injection nozzle 90, it cannot carry out the back titration functionally.

The Karl Fischer titration apparatus that is incorporated with both the volumetric titration device and the coulometric titration device is put on the market. In this case, operation units such as a display, a keyboard, and the like are shared with both device, but measurement units (the injection nozzle+detection electrode, or electrolytic electrode+detection electrode: but the detection electrode can be shared) are constituted exclusively. Such device, however, is configured so that the independent two methods are merely carried out by the shared operation units, and it is not provided with a unique function like the present invention as described hereinafter.

Prior art citations are Japanese Unexamined Patent Application Publication No. 06-308113 (Patent Literature 1) that discloses a combined type of titration apparatus for carrying out the volumetric analysis or the coulometric analysis, and Japanese Unexamined Patent Application Publication No. 2007-278919 (Patent Literature 2) that discloses a moisture meter for measuring the water content in the sample by the volumetric titration method or the coulometric titration method.

CITATION LIST

Patent Literature 1: Japanese Unexamined Patent Application Publication No. 06-308113
Patent Literature 2: Japanese Unexamined Patent Application Publication No. 2007-278919

SUMMARY OF INVENTION

Technical Problem

The above two conventional methods are processed by quite different steps from each other, and do not share any common components to be used except the detection electrode. This is caused by the coulometric titration apparatus and the volumetric titration apparatus that are used in general, as described hereinafter.

The titer is the water content that reacts with the iodine in the specific amount of Karl Fischer reagent. Accordingly, the water content to react with the Karl Fischer reagent is specified by means of a liquid to be a standard as water (standard solution), which is determined as the titer.

The titer determination seems in principle to be equivalent to a measurement of the quantity of electricity when the iodine ions are produced from the iodine included in the specific amount of Karl Fischer reagent by the electrolytic treatment for the specific amount of Karl Fischer reagent, (the electrolytic treatment for producing the iodine ions from the iodine is referred to the back coulometric titration, hereinafter).

However, when the amount of iodine is calculated using the electrolytic electrodes provided to the coulometric titration apparatus based on the quantity of electricity consumed by means of the conventional current control method, the calculated amount does not match with an actual amount of the iodine.

Meanwhile, the back coulometric titration means that the iodine ions are produced from the iodine. Accordingly, even in the conventional coulometric titration apparatus, it seems to be possible to carry out the back titration, that is, the remained iodine is put back to the iodine ions by means of the back coulometric titration after the iodine ions are produced from the iodine by means of the coulometric titration.

As described above, however, when the back coulometric titration is carried out in the conventional coulometric titration apparatus by means of the current control method, the calculated water content (the amount of iodine) does not match with the theoretical value. This is very inconvenient. Therefore, in the present circumstances, when the back titration is required, it is carried out in the volumetric titration apparatus by means of the volumetric titration method. There is a disadvantage that the back titration cannot be carried out in the coulometric titration apparatus without the burette and the injection nozzle.

Moreover, in order to reproduce the Karl Fischer reagent that has been used to the volumetric titration, it is necessary to change the iodine ions back to the iodine. In this case, the reproduction of the Karl Fischer reagent can be possible theoretically by the coulometric titration for producing the iodine from the iodine ions by means of the electrolytic electrode. But, the volumetric titration apparatus is not originally provided with the electrolytic electrodes, so that the used Karl Fisher reagent is disposed in fact because it cannot be reproduced.

In view of the above-mentioned problems in the conventional arts, the present invention has an object to provide a Karl Fischer titration method for carrying out the precise titration by the back coulometric titration, the back titration and the titer determination by means of the coulometric titration method, and a Karl Fischer apparatus for changing the coulometric titration with the back coulometric titration and changing the coulometric titration method with the volumetric titration method.

Solution to Problem

The present invention is assumed that a Karl Fischer titration method uses a Karl Fischer titration apparatus having a titration flask that is provided with electrolytic electrodes.

After forming a state that iodine exists in a solution contained in the titration flask, iodine ions are produced from the iodine at a anode of the electrolytic electrodes by means of a back coulometric titration.

When the solution is a dehydrated solvent including Karl Fischer reagent to be used to a volumetric titration, the back coulometric titration is performed in order to determine the titer of the Karl Fischer reagent, and the titer is determined based on a quantity of electricity consumed during the back coulometric titration.

As a result of the coulometric titration by means of the coulometric titration method using the electrolytic electrodes, when the solution is a anolyte in which the iodine remains, the back coulometric titration is performed for the anolyte in which the iodine remains, and the water content in the sample put in the titration flask is found based on the quantity of electricity consumed during the coulometric titration and the quantity of electricity consumed during the back coulometric titration.

As a result of the titration of the Karl Fischer reagent by means of the volumetric titration, when the solution is a dehydrated solvent in which the iodine remains, the back coulometric titration is performed for the dehydrated solvent in which the iodine remains, the water content in the sample put in the titration flask is found based on the added amount of the Karl Fischer reagent during the volumetric titration and the quantity of electricity consumed during the back coulometric titration. As a matter of course, at this time, the injection nozzle for the volumetric titration is provided to the titration flask, in addition to the electrolytic electrodes.

The apparatus of the present invention comprises an electrolysis control unit for changing the coulometric titration and the back coulometric titration. In addition, in order to change the volumetric titration and the back coulometric titration, the apparatus is provided with a changing control unit.

In the titration method using the apparatus with the electrolytic electrodes and the injection nozzle, the volumetric titration is performed till the water content in the sample put in the titration flask becomes a specific value, and it is changed to the coulometric titration when the water content becomes the specific value or less. The change of the volumetric titration and the coulometric titration is carried out by the changing control unit.

In the present invention, the coulometric titration is performed in the dehydrated solvent including the Karl Fischer reagent that has been used to the volumetric titration and contains the iodine ions, so that the Karl Fischer reagent can be revived by making the solvent in a state that the iodine ions reduced.

Advantageous Effects of Invention

According to the above, the Karl Fischer reagent to be used to the volumetric titration is put in the dehydrated solvent, and the solvent is subjected to the back coulometric titration to produce the iodine ions from the iodine. According the quantity of electricity consumed during the back coulometric titration, the titer of the reagent can be determined. The system does not require the standard solution to be used in conventional art.

The volumetric titration or the coulometric titration allows the specific amount of iodine to exist in the sample put in the specific solution (the dehydrated solvent at the volumetric titration; the anolyte at the coulometric titration), and at the point when the reaction of the water content in the sample and the iodine is terminated, the iodine ions can be produced from the excessive iodine that did not react with the water content in the sample by the coulometric titration, whereby the back titration can be performed at the coulometric titration, though the back titration has been carried out only at the volumetric titration of the conventional art.

In order to carry out the back titration by means of the conventional volumetric titration, the apparatus must be provided with a burette that contains the reagent (water-methanol) having a determined titer, but the present invention does not require it.

When the apparatus is configured to be provided with the electrolysis control unit for changing the coulometric titration and the back coulometric titration as necessary, the titration that has been used in usual or the above-mentioned each kinds of titrations can be performed independently or changing to another titration. When the sample contains high water content, by using the changing unit for changing the volumetric titration and the coulometric titration, the volumetric titration (or both the volumetric titration and the coulometric titration) is performed at the early stage of the titration, and the coulometric titration is performed near the end point of the titration. In such manner, the titration operation can be done in a short time. It is possible to reduce the operator's burden by automatically changing the titrations.

Though the electrolytic electrodes can be used at any time, the coulometric titration is performed in the dehydrated solvent including the Karl Fischer reagent that has been used to the volumetric titration, and the electrolytic treatment is carried out excessively to put the iodine ions back to the iodine, so that the Karl Fischer reagent can be revived. The used Karl Fischer reagent, which is always disposed, can be reused.

DESCRIPTION OF EMBODIMENTS

Principle

In the coulometric titration by means of a popular Karl Fischer titration apparatus as shown in FIG. 9, a side of the anolyte is an anode, and a side of catholyte through a membrane is a cathode. As long as the coulometric titration is carried out by applying a positive voltage on the anode and a negative voltage on the cathode, that is to say, as long as the iodine is produced from the iodine ions, the amount of the produced iodine can be calculated based on the quantity of electricity obtained by the appropriate current control.

Where the iodine ions are produced from the iodine by means of the back coulometric titration applying the negative voltage on the anode and the positive voltage on the cathode, the amount of the iodine ions produced by the current control does not match with the theoretical value, so that it cannot be applied to the titer determination and the determination of water content as described hereinafter.

Figure 2:
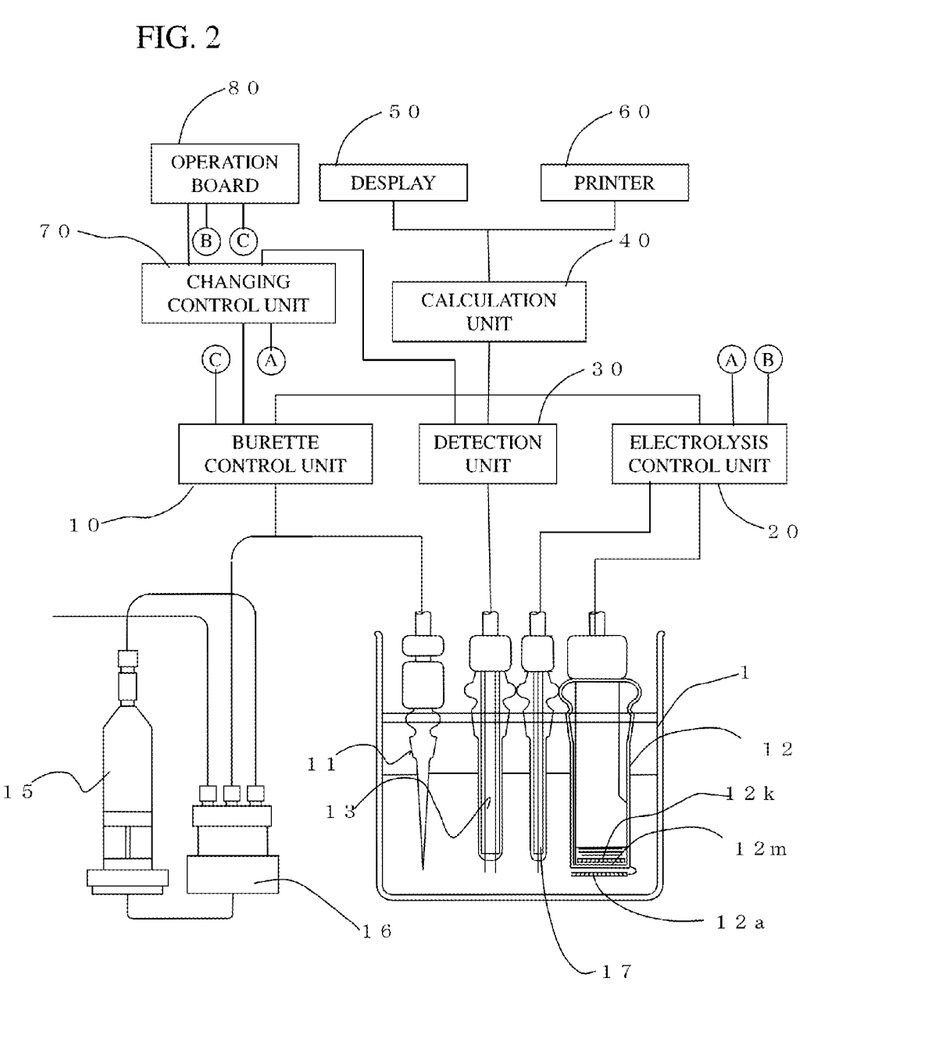
FIG. 2 is a sectional view of apparatus of the present invention.
Figure 3:
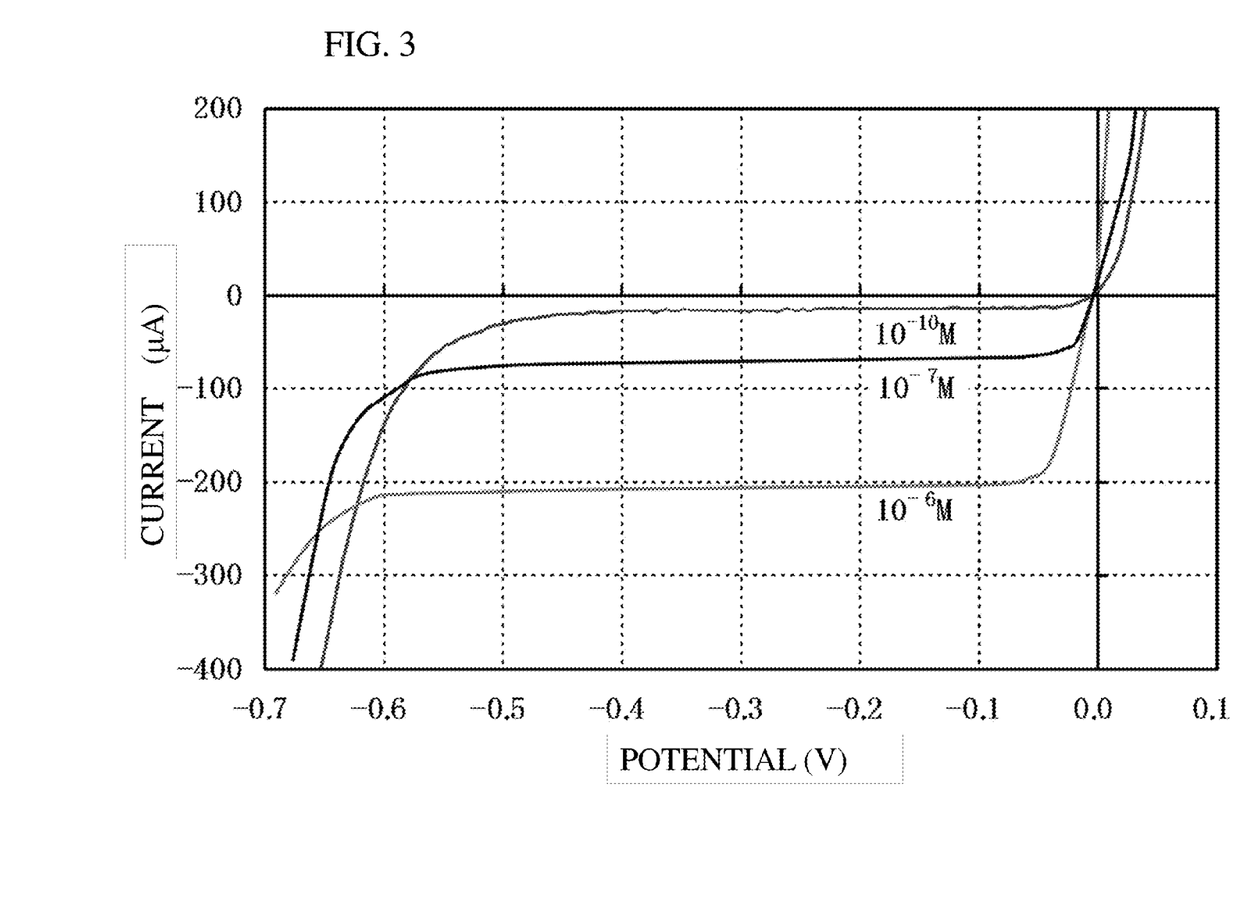
FIG. 3 is a graph showing a principle of the present invention.

So, a confirmation shown in FIG. 3 is made here. The back coulometric titration is carried out using a specific solution containing a known amount of iodine (the anolyte or dehydrated solvent). The current is measured while changing the potential between the electrodes. A relation between the current and the potential for every iodine concentration ($10^{-10}$M, $10^{-7}$M, $10^{-6}$M:M=mol/L) is shown in FIG. 3. Here, the current is a current that flows between a cathode (12$k$ in FIG. 2) and an anode (12$a$ in FIG. 2), and the potential is a potential between a reference electrode (17 in FIG. 2) and the anode.

It can be understood that an area where the current between the cathode and the anode is kept constant regardless of the potential change (−0.1V to −0.5V) exists in an area where the negative potential between the reference electrode and the anode is low, and the current changes suddenly against the potential when the negative potential gets higher. In addition, the value of the constant current gets large in a negative direction when the concentration of the iodine increases, however, a range of potential corresponding to the constant current does not change according to the concentration of the iodine.

The potential area where the current is constant is considered as a potential area where the iodine is reacting at a constant speed and changing to iodine ions according to the applied quantity of electricity, while the area where the current changes suddenly against the potential is considered as an area where negative ions except the iodine ions are produced.

Therefore, in order to use the back coulometric titration, the back coulometric titration should employ the potential control method using the area where the current is constant against the change of the potential (the current control to keep the potential constant or to keep the potential be in the above-mentioned area). In fact, by applying the potential control method to the titer determination and the back coulometric titration as described hereinafter, it is possible to ensure the matching between the produced amount of iodine ions and the applied quantity of electricity.

Even in the potential control method, when using the potential existing out of the area where the constant current is kept against the change of the potential, the produced amount of the iodine ions does not match with the theoretical value, which is not suitable to the titer determination and the water content determination, like the conventional art.

<Apparatus>

Figure 1:
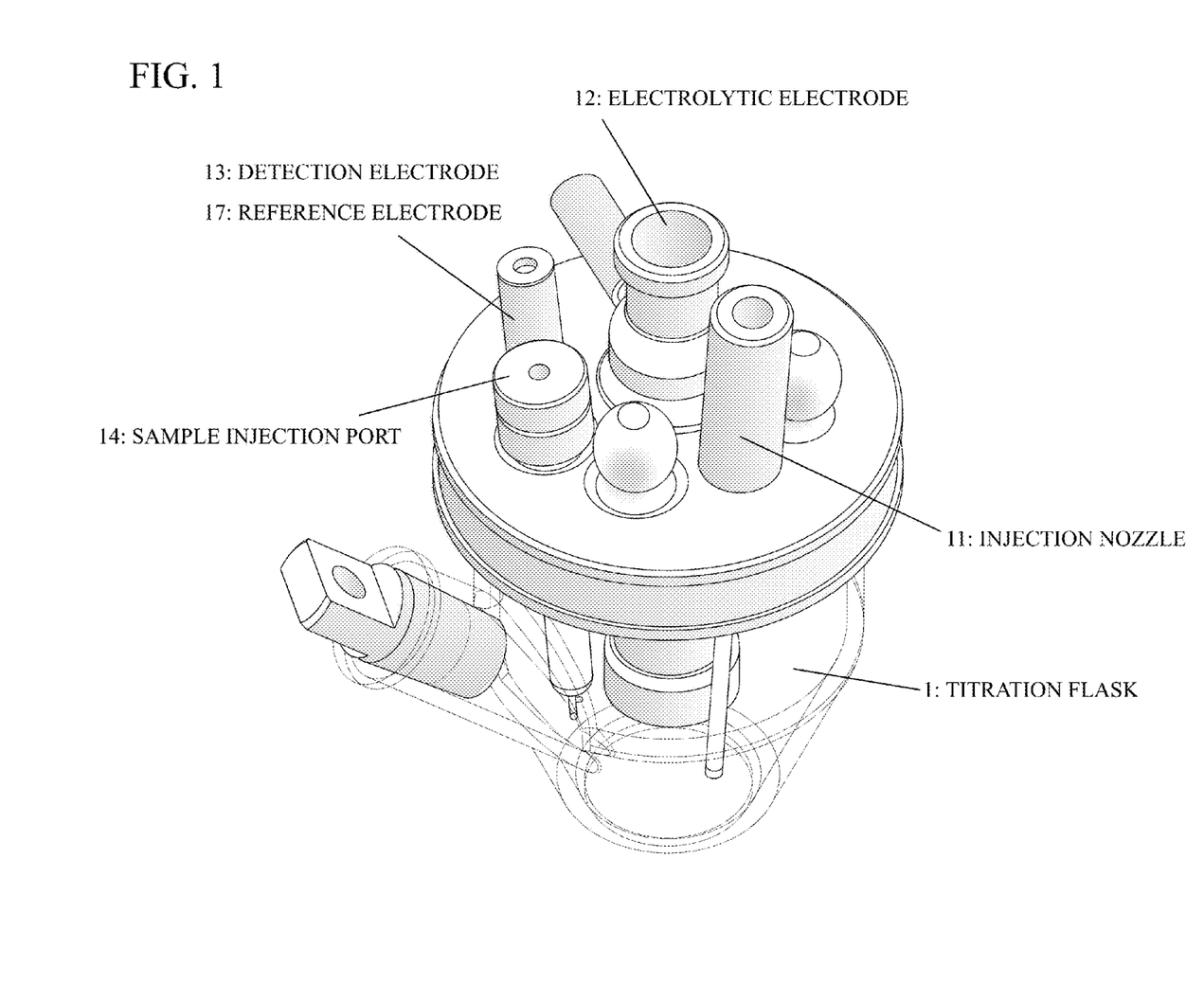
FIG. 1 is a perspective view showing apparatus of the present invention.

Based on the above confirmations, the present invention is constituted as shown in FIG. 1.

FIG. 1 is a perspective view of Karl Fischer titration apparatus designed based on the above described facts. FIG. 2 is a sectional view of the apparatus.

A titration flask 1 is configured to be provided with a sample injection port 14 (not shown in FIG. 2) as well as an injection nozzle 11 for the volumetric titration, electrolytic electrodes 12 for the coulometric titration, a detection electrode 13 for detecting the polarization state and an end point, and a reference electrode 17 for the potential control. A reagent supplied from a burette 15 is put in the titration flask 1 via the injection nozzle 11, and the reagent in the burette 15 is supplied from a reagent bottle (not shown). The apparatus is provided with a switching cock 16 for changing a path from the reagent bottle to the burette 15 with a path from the burette 15 to the injection nozzle 11. The apparatus is provided with a burette control unit 10 for controlling the amount of reagent to be supplied from the burette 15 to the injection nozzle 11.

The electrolytic electrodes 12 are arranged so that a anode 12a and a cathode 12k face each other across a membrane 12m. The anode 12a is released in the titration flask 1 and the cathode 12k is contacting with catholyte.

The detection electrode 13 and the reference electrode 17 are formed in one unit as shown in FIG. 1, but FIG. 2 shows them separately in order to be easily understandable, whereby the relations between the above-mentioned electrodes are defined clearly.

In the configuration, the anolyte is put into the titration flask 1, and the catholyte is put into the electrolytic electrodes 12. When the positive voltage is applied on the anode 12a and the negative voltage is applied on the cathode 12k (the coulometric titration), the iodine is produced from the iodine ions in the anolyte. The produced iodine reacts with the water in the sample added to the anolyte, which is controlled by an electrolysis control unit 20.

The detection electrode 13 detects the concentration of the iodine in the titration flask 1. That is to say, when the sample including the water is put in the solution (the volumetric titration: the dehydrated solvent, the coulometric titration: the anolyte) in the titration flask 1, the concentration of the iodine reduces, the voltage at the detection electrode 13 increases. On the contrary, when the concentration of the iodine in the solution increases by the titration, the voltage at the detection electrode 13 reduces.

Therefore, it is possible to determine the status of the titration based on the voltage indicated by the detection electrode 13. When the voltage indicated by the detection electrode 13 becomes a value indicating the end point of the titration, the burette control unit 10 or the electrolysis control unit 20 stops the titration, and the voltage or the end-point voltage at the detection electrode 13 during the titration is displayed on a display 50 or printed out by a printer 60.

It is nevertheless to say that the volumetric titration and the coulometric titration can be performed by means of the apparatus having the above-mentioned configuration, in the same manner as the conventional apparatus. In addition, it is possible to perform processing unique to the present invention as described hereinafter.

<The Volumetric Titration>

The volumetric titration method is processed as following steps.

First, the dehydrated solvent is injected in the titration flask 1. If the solvent contains the water, it is not possible to accurately measure the water content in the sample (described later). So the dehydrated solvent is dehydrated by titrating Karl Fischer reagent through the injection nozzle 11 (the voltage at the detection electrode 13 gets a specific value and less). Next, the sample is put in there, and Karl Fischer reagent is titrated while the burette control unit 10 is controlling the amount of Karl Fischer reagent titrated from the injection nozzle 11. The iodine in the Karl Fischer reagent reacts with the water in the sample and produces the iodine ions, so that the voltage detected at the detection electrode 13 falls.

Continuing the injection of Karl Fischer reagent and the detected voltage falls to the specific value, which is defined as the end point.

Since the iodine in Karl Fischer reagent reacts with the water by 1:1 (unit:mol), a calculation unit 40 can calculate the water content in the sample based on the additional amount of the reagent obtained from the burette control unit 30, when the voltage indicating the polarization state obtained by the detection unit 10 becomes the specific value. The result is displayed on the display 50.

The above-mentioned operation steps are the same as the conventional volumetric titration method.

<Titer Determination>

Karl Fischer reagent has a property of reducing its titer during storage. Accordingly, it is necessary to measure the water content (titer) reacting with the specific amount (1 ml) of the Karl Fischer reagent in advance of the titration.

The previous titration operation is usually done by using the standard solution as described above, but the above-mentioned back coulometric titration using the electrolytic electrodes 12 is employed here. That is to say, when the back coulometric titration is carried out by applying the negative voltage on the anode 12a and the positive voltage on the cathode 12k of the electrolytic electrodes 12, the iodine in Karl Fischer reagent is changed to the iodine ions.

Figure 4:
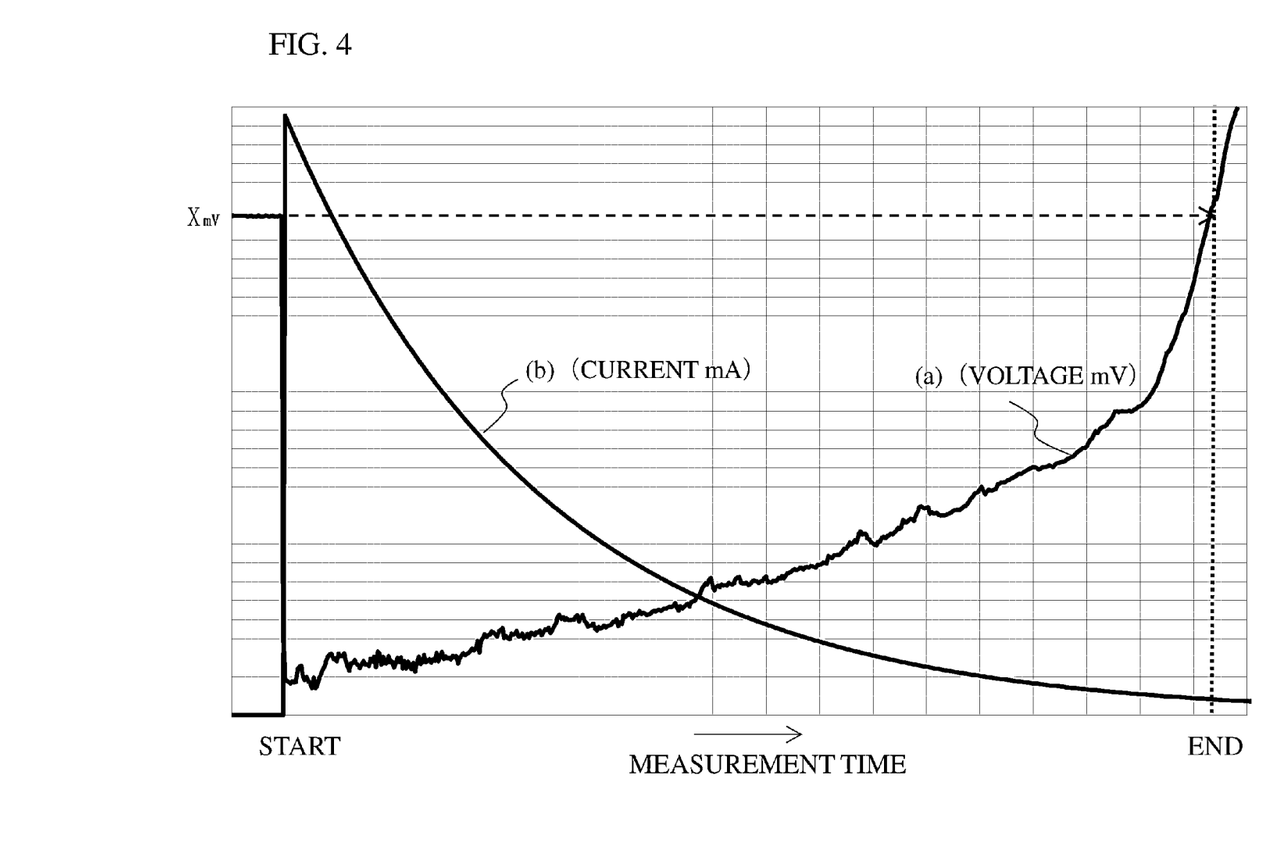
FIG. 4 is a graph showing a status that the titer is measured in the present invention.

As a result, the voltage indicated by the detection electrode 13 increases gradually (FIG. 4, (a)) and the flowing current reduces (FIG. 4, (b)) as shown in FIG. 4. The calculation unit 40 can calculate the titer based on the quantity of electricity obtained by the electrolysis control unit 20 before a point when the voltage indicated by the detection electrode 13 becomes the specific value XmV.

As described in the above <Principles>, the potential control method is employed here, and the current between the cathode 12k and the anode 12a is controlled so that the potential at the reference electrode 17 be in a specific range (e.g. $-0.5$ to $-0.1V$ as shown in FIG. 3). When the potential is out the range, the obtained titer does not match with the theoretical value. It is very inconvenient.

Table 1 shows results that the titer is measured by the back coulometric titration of the present invention. Regarding Karl Fischer reagent with titer 3.0 ($H_2O$ mg/mL) and Karl Fischer reagent with titer 1.0, the titers were measured by using the conventional method (using the standard solution) in advance, and these were marked as a reacting weight 100. Next, the reagent is injected in the titration flask 1 (0.3 mL and 0.2 mL regarding titer 3.0; 1.0 mL; and 0.5 mL regarding titer 1.0), and the iodine ions are produced from the iodine by means of the back coulometric titration. The results obtained by the processing are shown in Table 1. As understood by Table 1, the titer determination by means of the potential control method is well-matched with that by using the conventional standard solution. It is understood that using the potential control method is correct.

Besides, as a matter of course, the specific amount of Karl Fischer reagent to be measured is put into the titration flask which contains the dehydrated solvent previously dehydrated.

TABLE 1

| | Karl Fischer reagent Titer 3.0 ($H_2O$mg/mL) | | Karl Fischer reagent Titer 1.0 ($H_2O$mg/mL) | |
|---|---|---|---|---|
| Injection Amount | 0.3 mL | 0.2 mL | 1.0 mL | 0.5 mL |
| Frequency 1 | 99.8 | 100.1 | 98.2 | 99.7 |
| 2 | 100.1 | 99.0 | 99.6 | 100.5 |
| 3 | 98.4 | 99.9 | 102.5 | 100.2 |

<Coulometric Titration>

In case where the coulometric titration is carried out by means of the apparatus in the present invention, the processing steps are the same as the conventional steps. That is to say, after injecting the anolyte in the titration flask 1 and the catholyte in the electrolytic electrodes 12, the water content in the titration flask 1 is removed (dehydrated) by the coulometric titration of the electrolytic electrodes 12. In this condition, the sample is added in the anolyte. The coulometric titration is carried out by applying the positive voltage on the anode 12a and the negative voltage on the cathode 12k, which produces the iodine from the iodine ions in the anolyte by the current control method. The produced iodine reacts with the water in the sample. The concentration of the produced iodine can be detected by the detection electrode 13. When the voltage detected by the detection electrode 13 indicates the end point, the titration is terminated.

<Back Coulometric Titration>

The above-mentioned method is the same as the conventional coulometric titration method, but the apparatus in the present invention is possible to perform the back titration by means of the electrolytic electrodes.

Figure 5:
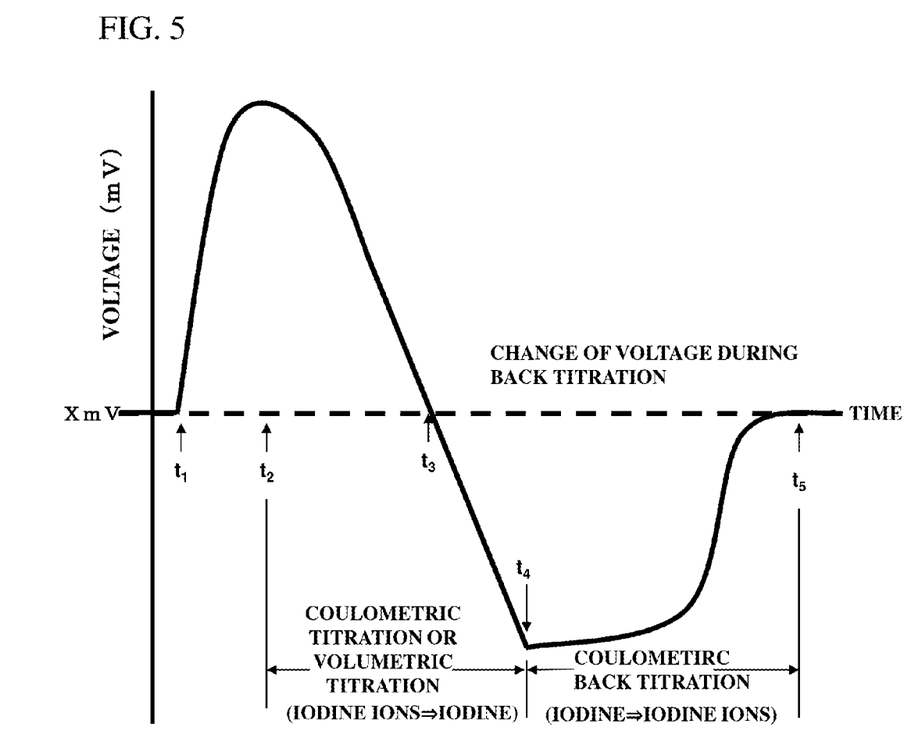
FIG. 5 is a graph showing a voltage change at the detection electrode when the coulometric titration is changed to the back coulometric titration.

As shown in FIG. 5, after a point (time $t_1$) when the sample is put in the titration flask 1 that contains the anolyte, the coulometric titration using the current control method is performed in response to an instruction to start the coulometric titration from the operation board 80, and supplies a constant current to the electrolytic electrodes 12 (time $t_2$), and then forms a state that a specific amount of iodine exists in the sample (in the anolyte). The reaction of the iodine with the water in the sample proceeds so that the voltage reaches the end point voltage (XmV) (time $t_3$). At this time, the coulometric titration is continued to form a state that the iodine is excessively existed (time $t_4$). Next, like the titer determination, the iodine ions are produced from the iodine by performing the back coulometric titration using the potential control method. Gradually, the concentration of the iodine reduces and the voltage at the detection electrode 13 increases. When the detected voltage becomes the specific end point voltage (VmX) (time $t_5$), the titration is terminated.

Where the quantity of electricity consumed at constant current during the coulometric titration is defined as Y, the quantity of electricity flowed during the back coulometric titration is defined as Z, and the quantity of electricity corresponding to the water content in the sample is defined as X, it becomes X=Y−Z, which can find the water content converted from the quantity of electricity X.

Table 2 shows the quantity of electricity consumed at the back coulometric titration, where the quantity of electricity consumed at the coulometric titration (producing iodine from iodine ions) for a specific time (in the current control method) is defined as 100. It is understood according to Table 2 that the quantity of the electricity at the back coulometric titration is well-matched with the quantity of the electricity at the coulometric titration.

In the measurement by means of the coulometric titration, there is a possibility that it takes a long time to react the iodine with the water content in the sample because the water content in the sample is hard to be dissolved in the anolyte. In the titration by means of the back coulometric titration, however, after the iodine excessively added by the coulometric titration is fully reacting with the water in the sample, the remained iodine is put back to the iodine ions, so that it is possible to carry out the quick and high-precise measurement.

The titration by means of this back coulometric titration is available to the volumetric titration method for forming the state that the specific amount of iodine exists in the sample. That is, the specific amount of Karl Fischer reagent is put into the titration flask 1 that contains the dehydrated solvent and the sample, which forms a state (time $t_4$, FIG. 5) that the specific amount of iodine exists in the sample in the dehydrated solvent. After that, the back coulometric titration is carried out by means of the potential control method using the electrolytic electrodes 12, whereby the iodine ions are produced from the iodine. According to the production of the iodine ions, the voltage at the detection electrode 13 increases. The detected voltage at this time becomes the specific end point (time $t_5$), and the titration is terminated. Therefore, the processing does not require the standard water-methanol.

TABLE 2

| | | The percentage (Y/Z) of the quantity of electricity (Y) during the back coulometric titration, when the quantity of electricity (Z) during the coulometric titration is 100 |
|---|---|---|
| Frequency | 1 | 98.4 |
| | 2 | 97.7 |
| | 3 | 98.4 |

Besides, in the above-mentioned method, the coulometric titration that is carried out before the back coulometric titration may be replaced with the volumetric titration, as described later.

<Reproduction of Reagent>

In the apparatus of the present invention, the Karl Fischer reagent used to the volumetric titration can be reproduced. The Karl Fischer reagent used to the volumetric titration is in a state that the iodine ions have been produced from the iodine.

In the apparatus to which the present invention is applied, the titration flask 1 is provided with the injection nozzle 11 for the volumetric titration and the electrolytic electrodes 12 for the coulometric titration. When the coulometric titration under the current control method is carried out in the titration flask 1 that contains the dehydrated solvent including the Karl Fischer reagent after the termination of the volumetric titration, the iodine is produced from the iodine ions, which means the reagent is revived.

After the reproduction treatment, the revived Karl Fischer reagent in the titration flask 1 is moved to an air-tight container like a reagent bottle, and injected again in the injection nozzle 11. In such way, the Karl Fischer reagent is recycled.

Accordingly, it is possible to reduce the consumed amount of Karl Fischer reagent to be injected in the injection nozzle 11. If the consumed amount of Karl Fischer reagent can be reduced, there is no need of a new purchase of the amount equivalent to the reduced consumption of Karl Fischer reagent. It is possible to reduce the overall cost for the volumetric titration.

<Coulometric Titration and Back Coulometric Titration>

As described above, the apparatus of the present invention enables to the coulometric titration and the back coulometric titration by means of the electrolytic electrodes 12. The electrolysis control unit 20 is to change the polarities of the electrolytic electrodes as necessary. For instance, the operation keyboard 80 is provided with keys, such as, "coulometric titration", "titer", "reproduction", and "volumetric titration." Those are controlled as follows: when the "coulometric titration" key or the "reproduction" key is pressed down, the coulometric titration is carried out applying the positive voltage on the anode 12a and the negative voltage on the cathode 12k; and when the "titer" key is pressed down, the back coulometric titration is carried out applying the negative voltage on the anode 12a and the positive voltage on the cathode 12k.

It is nevertheless to say that the apparatus can be configured to automatically change the coulometric titration by means of the coulometric titration method and the back coulometric titration. The operation keyboard 80 is provided with a "back titration" key by means of the coulometric titration, which is controlled as follows: when the key is pressed down, the electrolytic control unit 20 carries out the coulometric titration till the specific voltage (time $t_4$) over the end point, and then changes to the back coulometric titration.

<Volumetric Titration and Coulometric Titration>

It is configured that, when the "volumetric titration" key is pressed down from the operation keyboard 80, the burette control unit 10 is activated and the volumetric titration like the conventional manner is carried out. It is also configured that the volumetric titration (or a combination of the volumetric titration and the coulometric titration) is used at an early stage, and the coulometric titration is used near the end point. That is to say, it means that the concentration of the water is large when the voltage detected by the detection electrode 13 is high. When the detected voltage at the detection electrode 13 is more than the specific value, a changing control unit 70 activates the burette control unit 10 (or both the burette control unit 10 and the electrolysis control unit 20), and starts the volumetric titration (or start concurrently both the volumetric titration and the coulometric titration together). Otherwise, when the voltage detected by the detection voltage 13 becomes the specific value {that is a little higher than the end point voltage of FIG. 5 (at a point that is a little earlier than time $t_4$)}, the electrolysis control unit 20 is activated (only the electrolysis control unit 20 is activated), and starts the coulometric titration only.

The processing is discussed hereinafter according to FIG. 6.

Figure 6:
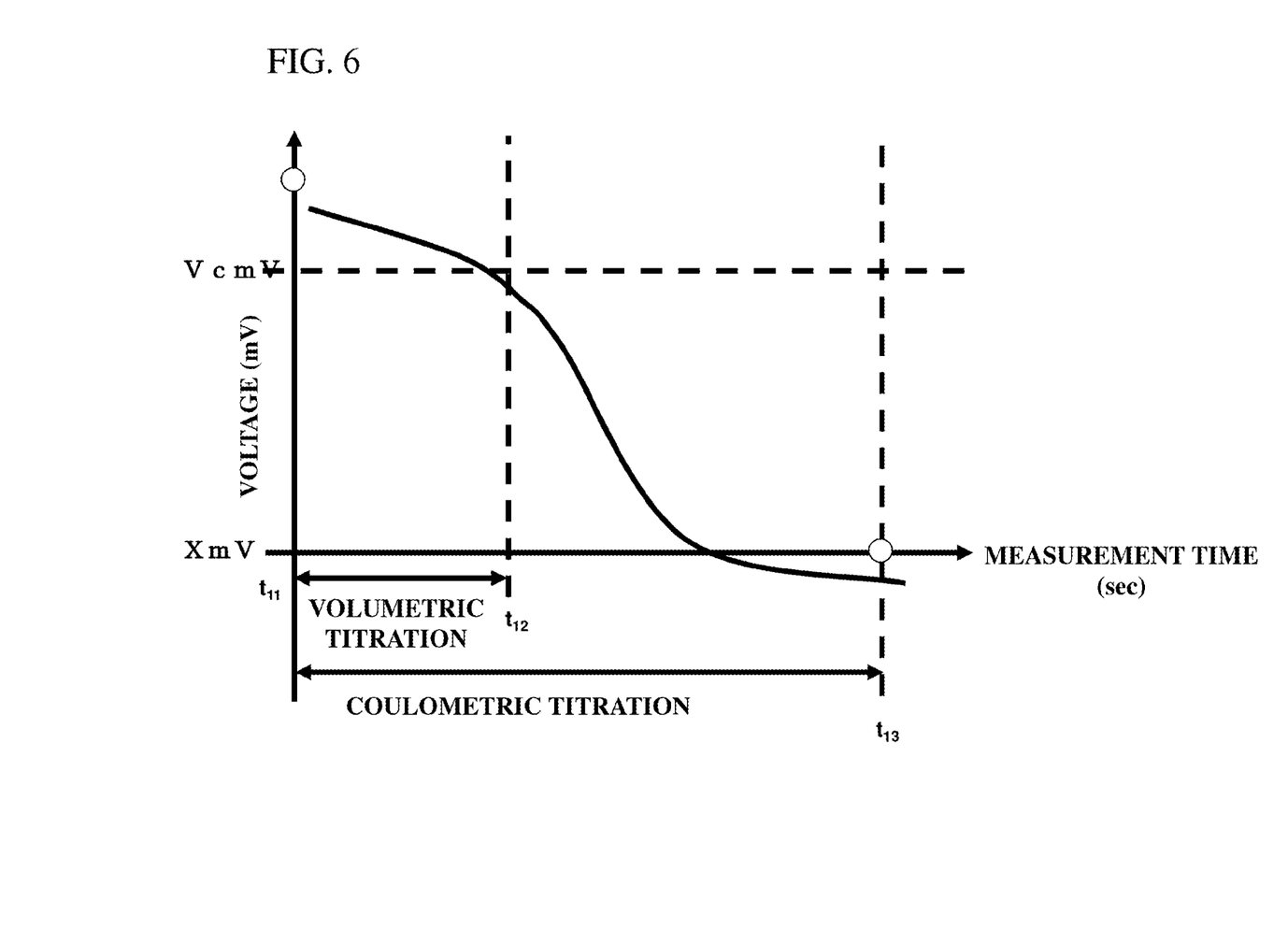
FIG. 6 is a graph showing a voltage change at the detection electrode when the volumetric titration is changed to the coulometric titration.

As shown in FIG. 6, the sample is put in the titration flask 1 that contains the dehydrated solvent (or the anolyte), and an instruction to start the volumetric titration is given from the operation board 80. Upon receipt of the instruction, the burette control unit 10 is activated (time $t_{11}$, FIG. 6), and starts to add the Karl Fischer reagent through the injection nozzle 11 for volumetric titration.

The water content in the dehydrated solvent reduces by the volumetric titration, and the voltage indicated by the detection electrode 13 reaches the specific value (VcmV) (time $t_{12}$, FIG. 6). At this point, the changing control unit 70 stops the working of the burette control unit 10, and the electrolysis control unit 20 is activated and changes to the coulometric titration.

After changing to the coulometric titration, the coulometric titration is continued till a point (time $t_{13}$, FIG. 6) when the voltage at the detection electrode 13 becomes the specific value (XmV) corresponding to the end point of the titration.

In the above description, since the volumetric titration has a property that the reaction speed with water is large but the accuracy is low, the volumetric titration is applied to the early stage of the titration that does not require the accuracy, whereby full use is made of the property. The coulometric titration has a property that the accuracy is high but the titration speed is inferior, and the coulometric titration is applied when the titration comes to near the end point, whereby full use is made of the property.

A changing voltage (VcmV), which regulates a timing to change from the volumetric titration to the coulometric titration, may be any value that is not less than the voltage at the titration end point. For example, it is preferable that the changing voltage (VcmV) is set to a voltage value that is from 50% to 90% of a first voltage detected at the beginning of the titration, and more preferable that it is set to a voltage value that is 80% of the first detected voltage. In such condition, the excessive water that is not concerned with a determination of the end point is allowed to react with the iodine in the Karl Fischer reagent at the volumetric titration, which can accelerate the titration speed, and a very small amount of water that is concerned with the specifying the end point is allowed to react with the iodine produced at the coulometric titration, which can realize the high accurate determination of the end point.

Figure 7:
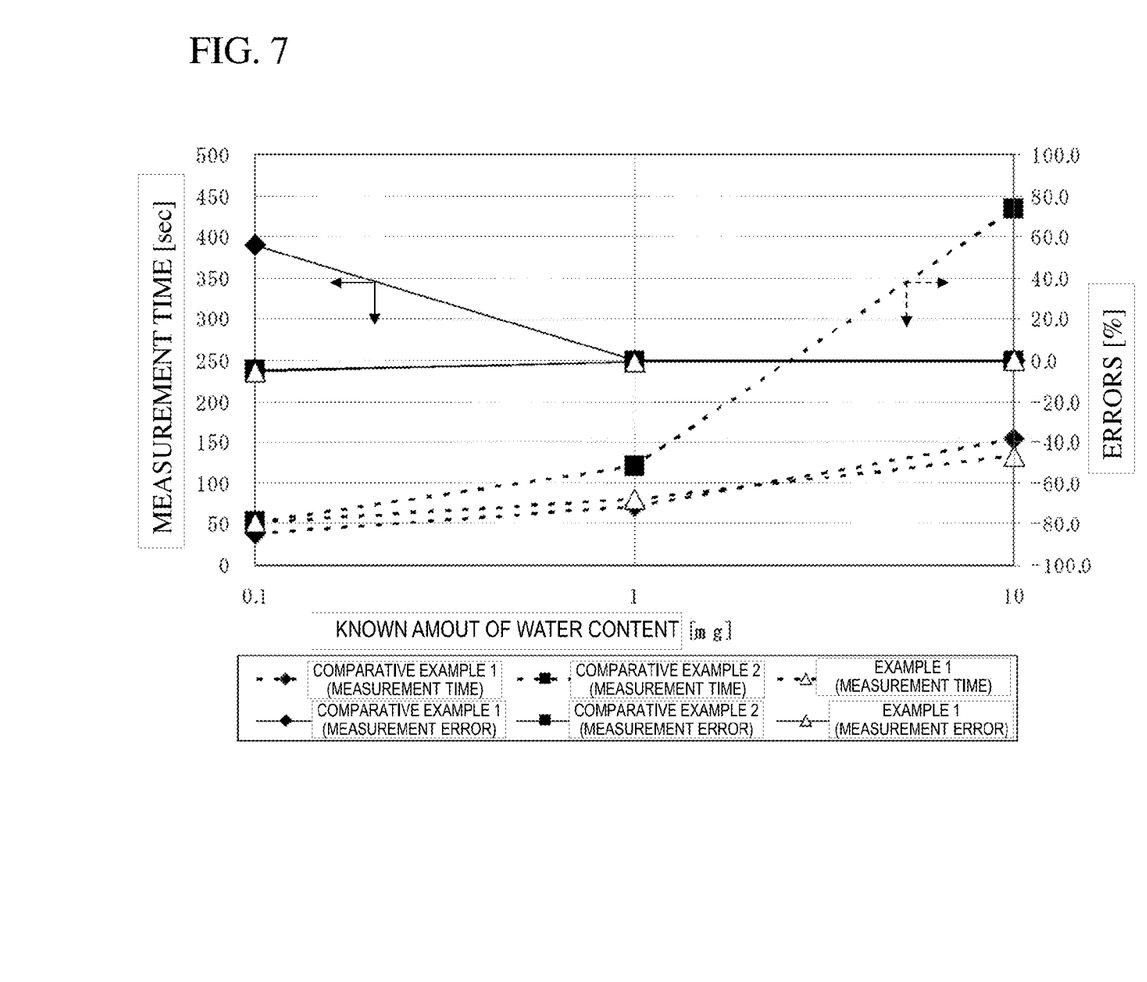
FIG. 7 is a graph showing measurement times and measurement errors for each water content in an example 1 and comparative examples 1 and 2.

Regarding the measurement time and measurement accuracy, FIG. 7 shows results when the above-mentioned process is carried out using a water standard.

The sample used here is the water standard 1.0 (titer 1:1 $mgH_2O/ml$) that a specific amount of water has been added to propylene carbonate in advance.

The water standard is generally used in order to check the accuracy of a moisture meter. There are three kinds of sampling amounts of the water standard that is used to the measurement of water content, that is, 10 ml=10 $mgH_2O$, 1 ml=1 $mgH_2O$, and 0.1 ml=0.1 $mgH_2O$. FIG. 7 shows averages of the measurement results when each sample is measured three times, and an example 1 shows the measurement results of the present invention when the volumetric titration is used at the beginning of the titration and the coulometric titration is used near to the end point, a comparative example 1 shows the measurement results when the volumetric titration is used only, and a comparative example 2 shows the results when the coulometric titration is used only.

As shown in FIG. 7, when the water content in the sample increases (over 1 mg, in particular) in the coulometric titration (the comparative example 2), the increasing rate of the measurement time becomes larger than the increasing rate of the water content. On the other hand, the measurement time in the example 1 of the present invention is almost linear like the volumetric titration (the comparative example 1). Therefore, in the example 1, even if the water content increases, the measurement can be carried out in the measurement time equivalent to the volumetric titration.

The volumetric titration (the comparative example 1) shows a tendency to lower the measurement accuracy when the water content is small (1 mg or less water content, in particular), but the measurement accuracy in the example 1 of the present invention shows the high accuracy same as in the coulometric titration (the comparative example 2). Accordingly, it is possible to ensure that the measurement accuracy in the example 1 is equal to that in the coulometric titration.

The above process employs the volumetric titration at the beginning of the titration and the coulometric titration near the end point, but it is possible to employ the volumetric titration and the coulometric titration at the beginning of the titration, and only the coulometric titration near the end point.

INDUSTRIAL APPLICABILITY

The present invention allows Karl Fischer titration apparatus to carry out the titer determination by the electrolytic treatment and the back titration, wherein the Karl Fischer reagent can be reproduced, as described above, so that the industrial applicability is very high.

REFERENCE SIGNS LIST

1 Titration flask
11 Injection nozzle
12 Electrolytic electrode
13 Detection electrode
14 Electrolysis control unit
17 Reference electrode

The invention claimed is:

1. A Karl Fischer titration method by means of a Karl Fischer titration apparatus having a titration flask provided with electrolytic electrodes including an anode and a cathode with a membrane therebetween, a detection electrode for detecting a polarization state of a solution in the titration flask, and a reference electrode for detecting a potential between the anode and the reference electrode, the method comprising steps of:
   forming a state that iodine exists in a solution contained in the titration flask;
   performing a back coulometric titration employing a potential control method to produce iodine ions from the iodine at the anode by flowing the current in an area where the current between the cathode and the anode is kept constant regardless of the potential change between the reference electrode and the anode while a minus potential is applied on the anode and a plus potential is applied on the cathode;
   terminating the back coulometric titration when the potential at the detection electrode is a specific value; and
   finding a water content corresponding to a quantity of electricity consumed during the back coulometric titration.

2. The Kari Fischer titration method according to claim 1, wherein the solution that the iodine exists is a dehydrated solvent including Karl Fischer reagent, and
   a titer of the Karl Fischer reagent is the quantity of electricity consumed during the back coulometric titration.

3. The Karl Fischer Titration method according to claim 1, wherein
   the state that the iodine exists in the solution is formed by reacting the iodine with water content in a sample put in anolyte by means of a coulometric titration for producing the iodine from the iodine ions in the anolyte contained in the titration flask, and;
   the step of finding the water content in the sample is based on the quantity of electricity consumed during the coulometric titration and the quantity of electricity consumed during the back coulometric titration.

4. The Karl Fischer Titration method according to claim 1, wherein
   the state that the iodine exists in the solution is formed by reacting water content in a sample put in a dehydrated solvent contained in the titration flask with iodine in Earl Fischer reagent by adding drops of the Karl Fischer reagent; and
   the step of finding the water content in the sample is based on the added amount of the Karl Fischer reagent and the quantity of electricity consumed during the back coulometric titration.

5. A Earl Fischer titration apparatus having a titration flask provided with electrolytic electrodes including an anode and a cathode with a membrane therebetween, a detection electrode for detecting a polarization state of a solution in the titration flask, and a reference electrode for detecting a potential between the anode and the reference electrode, the apparatus comprising:
   an electrolysis control unit for performing a coulometric titration to produce iodine from iodine ions at the anode by applying a plus potential on the anode and a minus potential on the cathode and a back coulometric titration employing a potential control method to produce the iodine ions from the iodine at the anode by flowing the current in an area where the current between the anode and the cathode is kept constant regardless the potential change between the reference electrode and the anode while a minus potential is applied on the anode and a plus potential is applied on the cathode; and;
   a changing unit for changing, as necessary, the coulometric titration and the back coulometric titration.

6. The Karl Fischer titration apparatus according to claim 5 further comprising:
   an injection nozzle for a volumetric titration that is provided to a titration flask; and
   a changing control unit for changing, as necessary, the volumetric titration using the injection nozzle and the coulometric titration or the back coulometric titration using the electrolytic electrodes.

7. A Karl Fischer titration method by means of the Karl Fischer titration apparatus in claim 6 comprising steps of:
   performing the volumetric titration till the water content in the sample put in the titration flask becomes a specific value;
   performing the coulometric titration when the water content becomes the specific value by the changing control unit; and
   terminating the titration when the potential at the detection electrode is a specific value.

8. A Karl Fischer titration method by means of the Karl Fischer titration apparatus in claim 6 comprising steps of:
   performing the volumetric titration together with the coulometric titration till the water content in the sample put in the titration flask becomes a specific value;
   performing the coulometric titration when the water content becomes the specific value by the changing control unit; and
   terminating the titration when the potential at the detection electrode is a specific value.

9. A Karl Fischer titration method by means of the Karl Fischer titration apparatus in claim 5 comprising steps of:
   performing the back coulometric titration for a dehydrated solvent after forming a state that the iodine exists therein by adding a specific amount of Karl Fischer reagent the a dehydrated solvent;
   terminating the titration when the potential at the detection electrode is a specific value; and
   determining a titer of the Karl Fischer reagent based on the quantity of electricity consumed during the back coulometric titration.

10. A Karl Fischer titration method by means of the Karl Fischer titration apparatus in claim 5 comprising steps of:
    performing the volumetric titration be adding the Karl Fischer reagent to a dehydrated solvent;
    returning the iodine ions in the dehydrated solvent to the iodine by changing to the coulometric titration by the changing control unit when the volumetric titration ends; and
    reviving the Kar Fischer reagent by stopping the current when the potential at the detection electrode becomes a specific value.

11. A Karl Fischer titration method by means of the Karl Fischer titration apparatus in claim 5 comprising steps of:
    reacting the iodine with the water content in the sample put in the anolyte by means of the coulometric titration for producing the iodine from the iodine ions in the anolyte contained in the titration flask;
    performing the back coulometric titration by the changing unit when it becomes a state that the iodine remains in the anolyte;
    stopping the back coulometric titration when the potential at the detection electrode becomes a specific value; and finding the water content in the sample based on the quantity of electricity consumed during the coulometric titration and the quantity of electricity consumed during the back coulometric titration.

12. A Karl Fischer titration method by means of the Karl Fischer titration apparatus in claim 6 comprising steps of:

reacting the iodine in the Karl Fischer reagent with the water content in the sample put in a dehydrated solvent by adding the Karl Fischer reagent to the dehydrated solvent;

performing the back coulometric titration by the changing unit when it becomes a state that the iodine exists in the dehydrated solvent;

stopping the back coulometric titration when the potential at the detection electrode becomes a specific value; and finding the water content in the sample based on the amount of the Karl Fischer reagent for the volumetric titration and the quantity of electricity consumed during the back coulometric titration.

* * * * *